United States Patent [19]

Klein

[11] 4,140,710

[45] Feb. 20, 1979

[54] RECOVERY OF o-CHLOROBENZILIDENE MALONONITRILE FROM FINELY DIVIDED MIXTURES THEREOF WITH COLLOIDAL SILICA

[75] Inventor: Joel M. Klein, Baltimore, Md.

[73] Assignee: The United States of America as represented by the Secretary of the Army, Washington, D.C.

[21] Appl. No.: 930,082

[22] Filed: Aug. 1, 1978

[51] Int. Cl.$^2$ ............................................. C07C 121/70
[52] U.S. Cl. .................................................. 260/465 G
[58] Field of Search ..................................... 260/465 G

[56] References Cited

U.S. PATENT DOCUMENTS

| 3,549,683 | 12/1970 | Rosin | 260/465 G |
| 3,963,770 | 6/1976 | Knapp | 260/465 G |

*Primary Examiner*—Dolph H. Torrence
*Attorney, Agent, or Firm*—Nathan Edelberg; Harold H. Card, Jr.; A. Victor Erkkila

[57] ABSTRACT

A method of recovering o-chlorobenzilidene malononitrile from finely divided particulate mixtures thereof with colloidal silica. The mixture is contacted with a solvent such as methylene chloride, in which the o-chlorobenzilidene malononitrile is highly soluble and the colloidal silica is insoluble, the resulting solution is filtered to remove the insoluble colloidal silica, and the o-chlorobenzilidene malononitrile is crystallized from the filtrate.

6 Claims, No Drawings

4,140,710

RECOVERY OF O-CHLOROBENZILIDENE MALONONITRILE FROM FINELY DIVIDED MIXTURES THEREOF WITH COLLOIDAL SILICA

GOVERNMENTAL INTEREST

The invention described herein may be manufactured, used and licensed by or for the Government for governmental purposes without the payment to me of any royalties thereon.

BACKGROUND OF THE INVENTION

The U.S. Government has large stocks of CS1 and CS2, which were formerly employed as lachrymatory agents in burster-type projectiles, but are no longer required and under current plans must be destroyed. CS1 consists of CS, which is essentially o-chlorobenzilidene malononitrile, mixed with approximately 5% by weight of a colloidal silica. The term colloidal silica as used herein refers to extremely finely divided, porous water free silica ($SiO_2$), having a bulk density ranging about from 2 to 10 lbs./cu. ft. Such colloidal silicas when suspended in a liquid have an ultimate particle size ranging about from 10 to 50 millimicrons. These colloidal silica products are often employed as anticaking agents and as flatting agents for lacquers and are marketed under such trade names as Santocel® by Monsanto Chemical Co., Cab-o-Sil® by Godfrey L. Cabot, Inc., and Syloid® by Davison Chemical Company.

In the manufacture of CS1 and CS2, the CS is micropulverized to particles ranging in size about from 5 to 10 microns and then blended in a tumbler mill or other suitable apparatus with the colloidal silica. In this manner, the colloidal silica is intimately mixed with the CS in such a manner that each particle of CS is coated at least partially with the colloidal silica, which functions as an antiagglomerating and free flow conditioning agent. Because the colloidal silica adheres to the CS particles by physical attraction forces, it is not possible to separate the CS from the colloidal silica by mechanical processes.

The military requires a CS product containing at least 96% o-chlorobenzilidene malononitrile for use in various riot control devices. However, the government supply is insufficient to meet the requirements for CS of such purity in these riot control devices, and the facilities previously employed to manufacture CS used to make CS1 and CS2 have been dismantled. For these reasons, the recovery of CS from CS1 and CS2 is desirable.

SUMMARY AND DETAILED DESCRIPTION OF THE INVENTION

An object of the present invention is to provide a process for recovering o-chlorobenzilidene malononitrile from finely divided mixtures thereof with colloidal silica.

Another object of the invention is to provide an efficient process for recovering CS from CS1 and CS2.

It has been found that the foregoing objects can be achieved in accordance with the process of the present invention, which comprises the following steps:

(1) dissolving the o-chlorobenzilidene malononitrile in a solvent, such as methylene chloride, in which the colloidal silica is insoluble;

(2) separating the colloidal silica from the resulting solution by filtration through a filter medium sufficient to retain the colloidal silica particles; and (3) separating the o-chlorobenzilidene malononitrile from the filtrate solution.

The successful operation of the process is essentially dependent on the use of a suitable solvent and an appropriate filter medium. I have found that methylene chloride ($CH_2Cl_2$) is a most desirable solvent because of its (a) high solvent power for o-chlorobenzilidene malononitrile and low solvent power for impurities, and (b) efficiency for separating the o-chlorobenzilidene malononitrile from the colloidal silica. However, other liquid solvents including methanol, ethanol, propanol and isopropanol and mixtures thereof, can be satisfactorily employed in the present process, although they possess a somewhat lower solvent power for o-chlorobenzilidene malononitrile than methylene chloride. Filter media which are suitable for separating the colloidal silica particles from lacquers wherein they are employed as flatting agents, can be effectively used to remove the colloidal silica particles from the CS solutions in the process of the present invention. For example, a filter medium as retentive as Whatman No. 4 filter paper is suitable for use on a small scale; while for large scale operations a filter press containing a filter bed, through which the solution is pumped under hydraulic pressure, can be employed. The o-chlorobenzilidene malononitrile can be separated from the filtrate solution preferably by crystallization or by removal of the solvent by distillation.

The following examples serve to illustrate specific embodiments of the method for carrying out the process of the present invention. However, they will be understood to be illustrative only and not to limit the invention in any manner.

EXAMPLE 1

25 grams of CS1 (an intimate mixture containing 90.1% by weight of o-chlorobenzilidene malononitrile and 4.2% by weight of silica in the form of Santocel®, a silica aerogel having a bulk density of about 6 lbs./cu. ft. and an ultimate particle size of 10–20 millimicrons, marketed by Monsanto Chemical Co.) was agitated with 100 milliliters of methylene chloride at about 40° C. until the CS was completely dissolved. The hot solution thus obtained was filtered through Whatman No. 4 filter paper to remove the undissolved Santocel®, and the filtrate was cooled to a temperature of about 10° C. to effect crystallization. The resulting crystals were separated by filtration and dried. The product thus obtained contained 96.9% o-chlorobenzilidene malononitrile (determined by GLC) and 0.4% silica.

The present process provides a subsidiary benefit in that the CS recovered from the process is of greater purity than the CS in the CS1 starting material, since the impurities are removed during the filtration step if they are not soluble in the solvent, or tend to remain in the mother liquor when the CS is crystallized from the solvent solution. Thus, the CS in the CS1 starting material employed in the foregoing example had a purity of 94.1% (determined by dividing the 90.1% by weight content of CS in the CS1 by the total % weight of material other than silica 95.8%), whereas the CS product produced by the present process had a purity exceeding 96%. (CS is usually manufactured by reacting o-chlorobenzilidene with malononitrile in alcoholic solution. Typical impurities in the resulting product include unreacted starting materials as well as hydrolysis and oxidation products. Further, CS degrades slightly on standing, giving rise to products which have not been completely identified. Since the inventory CS1 had been in storage for a number of years, there were more impurities in the CS than when the CS was first manufactured.)

EXAMPLE 2

When the procedure of Example 1 was repeated using a more retentive filter medium, Millipore filter paper type HAWG 047 (marketed by Millipore Corp.), the CS product contained 96.2% o-chlorobenzilidene malononitrile and 0.2% by weight silica.

EXAMPLE 3

25 grams of CS2 (a product identical to CS1 except that Santocel ® is replaced by Cab-o-Sil ®, a colloidal silica having a bulk density of approximately 2.3 lbs./cu. ft.) was agitated with 100 milliliters of methylene chloride heated to 40° C. until the CS was completely dissolved. The solution at about 40° C. was filtered as in Example 1 and the filtrate was cooled to below room temperature (about 10° C.) to crystallize the o-chlorobenzilidene malononitrile, which was then separated by filtration and dried. Approximately 18 grams of product containing 0.3% silica and over 96% o-chlorobenzilidene malononitrile were obtained. This exceeds the military specification of purity for CS, which requires a content of at least 96% by weight of o-chlorobenzilidene malononitrile.

The mother liquor thus obtained was recycled to dissolve further amounts of CS2. When the mother liquor became too concentrated for reuse, it was distilled to recover the solvent for recycling to the process. The residue after distillation contained o-chlorobenzilidene malononitrile mixed with silica and other impurities. The residual mixture was then placed in a suitable incenerator and burned.

Similar results can be obtained by employing methanol, ethanol, propanol or isopropanol in place of methylene chloride. Other solvents that can be employed in similar manner include acetone, dioxane, chloroform, carbon tetrachloride and ethylene chloride.

Thus, the present invention provides a number of significant advantages, including:

(a) CS can be recovered from CS1 and CS2 in excellent yield and purity.

(b) The solvents can be readily recovered and recycled, keeping costs at a minimum.

(c) The CS can be purified to the extent required to conform with the military specifications for the material.

(d) The invention utilizes existing resources to produce needed CS while simultaneously disposing of CS1 and CS2, which are no longer needed.

The foregoing disclosure and drawings are merely illustrative of the principles of this invention and are not to be interpreted in a limiting sense. I wish it to be understood that I do not desire to be limited to the exact details described, because obvious modifications will occur to a person skilled in the art.

What is claimed is:

1. A process of recovering o-chlorobenzilidene malononitrile from a finely divided particulate mixture thereof with colloidal silica, which comprises
    contacting the mixture with a solvent in which the o-chlorobenzilidene malononitrile is soluble and the colloidal silica is insoluble;
    separating the insoluble colloidal silica from the resulting solution by filtration through a filter medium sufficient to retain the colloidal silica; and
    separating the o-chlorobenzilidene malononitrile from the solution.

2. A process according to claim 1, wherein the particulate mixture consists essentially of o-chlorobenzilidene malononitrile having an average particle size range about from 5 to 10 microns, and colloidal silica having a bulk density ranging about from 2 to 10 lbs./cu. ft.

3. A process according to claim 1 or 2, wherein the solvent is at least one of the group consisting of methylene chloride, methanol, ethanol, propanol and isopropanol.

4. A process according to claim 3, wherein the solvent consists essentially of methylene chloride.

5. A process according to claim 3, wherein the particulate mixture contains about from 90% to 95% by weight of o-chlorobenzilidene malononitrile and about 5% by weight of colloidal silica.

6. A process according to claim 4, wherein the o-chlorobenzilidene malononitrile is separated from the solution by crystallization.

* * * * *